(12) United States Patent
Jayavanth et al.

(10) Patent No.: US 9,921,141 B2
(45) Date of Patent: Mar. 20, 2018

(54) CENTRIFUGAL MICROFLUIDIC DEVICE AND METHODS OF USE

(71) Applicant: KONINKLIJKE PHILIPS N.V., Eindhoven (NL)

(72) Inventors: Sanjay Jayavanth, Bangalore (IN); Payal Keswarpu, Bangalore (IN); Manoj Varma, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/419,486

(22) PCT Filed: Aug. 8, 2013

(86) PCT No.: PCT/IB2013/056479
§ 371 (c)(1),
(2) Date: Feb. 4, 2015

(87) PCT Pub. No.: WO2014/024154
PCT Pub. Date: Feb. 13, 2014

(65) Prior Publication Data
US 2015/0226652 A1    Aug. 13, 2015

(30) Foreign Application Priority Data

Aug. 8, 2012   (IN) .................. 3254/CHE/2012

(51) Int. Cl.
*G01N 15/06*   (2006.01)
*G01N 33/00*   (2006.01)
(Continued)

(52) U.S. Cl.
CPC ........ *G01N 1/4077* (2013.01); *B01L 3/50273* (2013.01); *B01L 2300/0806* (2013.01);
(Continued)

(58) Field of Classification Search
CPC ......... G01N 15/06; G01N 33/00; G01N 33/48
(Continued)

(56) References Cited

U.S. PATENT DOCUMENTS 5,594,164 A * 1/1997 Bull .............................. 73/61.66
6,302,134 B1   10/2001 Kellogg et al.
(Continued)

FOREIGN PATENT DOCUMENTS

CN      102565179 A    7/2012
EP        795129 B1    1/2001
(Continued)

OTHER PUBLICATIONS

Zhang et al.; "A lab-on-CD prototype for high-speed blood separation", 2008, vol. 18, pp. 1-6.

*Primary Examiner* — Brian J Sines

(57) ABSTRACT

Provided herein are systems and methods for separation of heterogeneous analyte. In some embodiments, the systems and methods herein utilize an analyte holding portion that receives a volume of analyte. The analyte holding portion may include an analyte receiving portion and a microfluidic separation channel, A rotatable carrier holding the analyte holding portion may be rotated by a rotational actuator so as to apply a centrifugal force to the volume of analyte such that the analyte is separated into at least two components.

13 Claims, 3 Drawing Sheets

(51) Int. Cl.
  *G01N 33/48* (2006.01)
  *G01N 1/40* (2006.01)
  *B01L 3/00* (2006.01)
  *G01N 21/78* (2006.01)
  *G01N 21/07* (2006.01)

(52) U.S. Cl.
  CPC ...... *B01L 2400/0409* (2013.01); *G01N 21/07* (2013.01); *G01N 21/78* (2013.01); *G01N 2001/4083* (2013.01)

(58) Field of Classification Search
  USPC .............. 422/68.1, 63, 72, 82.05, 502, 503; 436/43, 174, 45, 63, 164, 177
  See application file for complete search history.

(56) References Cited

U.S. PATENT DOCUMENTS

| | | | |
|---|---|---|---|
| 6,319,469 B1 * | 11/2001 | Mian et al. | 422/64 |
| 6,319,719 B1 * | 11/2001 | Bhullar et al. | 436/70 |
| 6,406,672 B1 * | 6/2002 | Bhullar et al. | 422/73 |
| 6,548,788 B2 | 4/2003 | Kellogg et al. | |
| 6,585,662 B1 | 7/2003 | Jones et al. | |
| 6,632,399 B1 | 10/2003 | Kellogg et al. | |
| 6,653,625 B2 | 11/2003 | Andersson | |
| 6,812,457 B2 | 11/2004 | Andersson | |
| 6,818,435 B2 | 11/2004 | Carvalho et al. | |
| 7,061,594 B2 | 6/2006 | Worthington et al. | |
| 7,094,354 B2 * | 8/2006 | Pugia et al. | 210/787 |
| 7,221,632 B2 | 5/2007 | Worthington | |
| 7,943,386 B2 | 5/2011 | Grumann | |
| 8,765,062 B2 * | 7/2014 | Linder et al. | 422/82.05 |
| 2003/0032064 A1 * | 2/2003 | Soller | A61B 5/14535 435/7.1 |
| 2003/0223913 A1 | 12/2003 | Karp et al. | |
| 2006/0263247 A1 | 11/2006 | Ozaki et al. | |
| 2006/0263265 A1 | 11/2006 | Kang et al. | |
| 2008/0280365 A1 * | 11/2008 | Grumann et al. | 436/70 |
| 2009/0004060 A1 | 1/2009 | Omuro et al. | |
| 2009/0298092 A1 | 12/2009 | Tsai et al. | |
| 2010/0130997 A1 | 5/2010 | LeVaughn et al. | |
| 2011/0104009 A1 | 5/2011 | Kawamura et al. | |
| 2011/0212432 A1 | 9/2011 | Torgersen et al. | |
| 2012/0109688 A1 | 5/2012 | Yoo | |

FOREIGN PATENT DOCUMENTS

| | | |
|---|---|---|
| JP | 7280814 A | 10/1995 |
| RU | 2253116 C2 | 5/2005 |

* cited by examiner

CENTRIFUGAL MICROFLUIDIC DEVICE AND METHODS OF USE

CROSS-REFERENCE TO PRIOR APPLICATIONS

This application is the U.S. National Phase application under 35 U.S.C. § 371 of International Application No. PCT/IB2013/056479, filed on Aug. 8, 2013, which claims the benefit Indian Patent Application No. 3254/CHE/2012, filed on Aug. 8, 2012. These applications are hereby incorporated by reference herein.

The present disclosure pertains to centrifugal microfluidic devices and methods for use thereof.

Determination of the levels of various substances in the body, such as, for example, glucose, electrolytes, cholesterol, or other substances, typically involves chemical analysis by technicians in a clinical lab. However, the ability to perform some of these common tests at point-of-care, bedside, or home environments (or otherwise through simple mechanisms that can be used in non-laboratory environments) may enable increased frequency of testing and thereby may assist in achieving better disease control, may help to keep patient costs down, and may provide other benefits. Many home or non-laboratory-based tests utilize "strip based" diagnostic tools (e.g., home pregnancy test kits). Generally these "strip-based" test kits are implemented using colorimetry, which utilizes immobilized reagents on a test strip that react with substances in a tested fluid (e.g., urine) to produce chromogenic (color producing) compounds that indicate the results of the test. These color change mechanisms can be generally visualized with the naked eye or, in some instances, may be measured more precisely with absorption spectrometers.

Color change test kits are easily visualized when used to test relatively transparent fluid samples such as, for example, urine or saliva. In the case of complex samples such as blood, however, the heterogeneous and colored nature of the fluid sample makes typical strip-based testing difficult. In laboratory settings, it may be necessary to separate the cellular contents (e.g., red blood cells, white blood cells) from blood plasma (which contains most of the substances tested for) before a colorimetric reaction or other analysis can be performed. This necessitates the use of separation technology to filter plasma from whole blood. However, this type of separation technology is not typically present in home-based settings or non-laboratory point-of-care settings (e.g., clinical settings lacking sophisticated laboratory equipment).

SUMMARY

Accordingly, it is an object of one or more embodiments described herein to provide a system for separation of a heterogeneous analyte, comprising: an analyte holding portion configured to receive a volume of analyte, the analyte holding portion including: an analyte receiving portion, and a microfluidic separation channel; and a rotatable carrier that holds the analyte holding portion and that is rotated by a rotational actuator so as to apply a centrifugal force to the volume of analyte such that the analyte is separated into at least two components.

It is yet another aspect of one or more embodiments to provide a method for separation of a heterogeneous analyte, comprising: loading a volume of analyte into an analyte holding portion that includes: an analyte receiving portion, and a microfluidic separation channel; and rotating a rotatable carrier in which the analyte holding portion is secured so as to apply a centrifugal force to the volume of analyte such that the analyte is separated into at least two components.

It is yet another aspect of one or more embodiments to provide a system for separation of a heterogeneous analyte, comprising: analyte holding means for receiving a volume of analyte, the analyte holding means including: an analyte receiving portion, and a microfluidic separation channel; and rotatable carrier means for holding the analyte holding means and for being rotated by a rotational actuator so as to apply a centrifugal force to the volume of analyte such that the analyte is separated into at least two components.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 1:
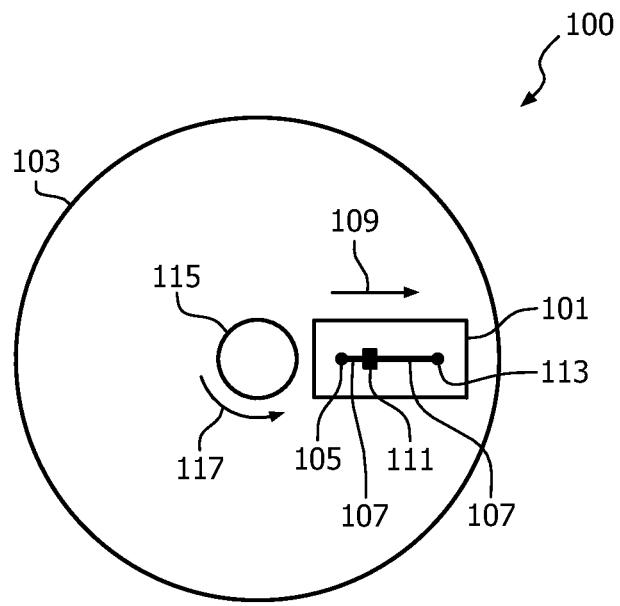
FIG. 1 is an example of at least a portion of a system for separation of a heterogeneous analyte, according to various embodiments of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Provided herein are systems, devices, and methods for separating a heterogeneous fluid sample using centrifugal force for the purposes of testing or measuring one or more characteristics of one or more components of the sample. In some embodiments, the systems, devices, and methods utilize small volumes of fluid (e.g., less than 50 μL of fluid), thereby facilitating ease of use, patient comfort (when the fluid is a bodily fluid, e.g., whole blood), simplicity of design, and/or providing other benefits. In some embodiments, commercial off-the-shelf home consumer products may be used in or with the systems, devices, and methods provided herein, so as to provide for diagnostics in home or non-laboratory settings.

In some embodiments, a system for separation of a heterogeneous analyte (or sample) may be provided. In some instances, the heterogeneous analyte may be or include a liquid analyte such as, for example, blood that comprises blood plasma with several biomarker proteins as well as red and white blood cells. FIG. 1 illustrates a system 100, which is an example of a system for separation of a heterogeneous analyte (e.g., blood). In some embodiments, system 100 may include an analyte holding portion 101, a rotatable carrier 103, and/or other elements.

In some embodiments, analyte holding portion 101 may include a planar object or chip made from glass, plastic, polycarbonate, polymer (e.g., Poly Dimethyl Siloxane (PDMS), Polycarbonate, PolyMethylMethacrylate (PMMA)), or other substance. For example, analyte holding portion 101 may include an analyte receiving portion 105, a separation channel 107, and/or other features. In some embodiments, analyte receiving portion 105 may include an exposed opening or reservoir in analyte holding portion 101 that is able to receive a quantity of liquid analyte. In some embodiments, the size of analyte receiving portion may be microfluidic in nature. Accordingly, in some embodiments, analyte receiving portion 105 may be sized so as to receive 50-100 μL of liquid analyte (or sample). Other volumes may be used. In some embodiments, an overflow area may be provided to receive excess analyte.

Analyte receiving portion 105 may be connected to separation channel 107 such that liquid analyte introduced into analyte receiving portion 105 may travel into separation channel 107. In some embodiments, separation channel 107 may be a capillary channel having microfluidic dimensions. For example, in some embodiments, separation channel 107 may have a cross-sectional diameter of about 1 mm, may have a channel height and width of about 1 mm, and/or may have other dimensions. In some embodiments, the volume of separation channel 107 is not substantially larger than sample input volume. For example, for an input volume of 50 μl, the length of separation channel 107 may be no longer than 5 cm.

When analyte is introduced into analyte receiving portion 105 and a force (i.e., a "separating force") is applied to analyte holding portion 101 in the direction of arrow 109, analyte may move into separation channel 107 and separate into its constituent components, with more massive components traveling farther down separation channel 107 in a shorter period of time. Accordingly, when the analyte is blood, red and white blood cells will separate from blood plasma by moving further down separation channel 107 than blood plasma. As described herein, it is desirable to separate red and white blood cells from blood plasma so as to perform analytic analysis on one or more characteristics of the blood plasma such as, for example, glucose level, electrolyte level, cholesterol level, and/or other characteristics. In some embodiments, separation channel 107 may include an analysis portion 111 which may be or include an enlarged area of separation channel and/or a window in analyte holding portion 101 having optical characteristics enabling spectrographic or other analysis (e.g., analysis portion 111 may be a generally transparent window that enables light to be transmitted therethrough so that said light may pass through analyte (i.e., a separated component thereof) within analysis portion 111). In some embodiments, analysis portion 111 need not be an enlarged portion, but may be a portion of separation channel 107 sized similar to other portions of separation channel 107.

In some embodiments, analyte holding portion 101 may include an end portion 113 that provides a reservoir wherein heavier separated components of the heterogeneous analyte can collect. In some embodiments, end portion 113 may include an enlarged area at the termination of separation channel 107. In some embodiments, end portion 113 may be microfluidic in size. For example, in some embodiments, end portion 113 may be sized so as to hold a volume of 50 μl to 2 ml of analyte. Other sizes may be used.

In some embodiments, rotatable carrier 103 may be or include a planar object to which analyte receiving portion 101 can be removably attached and which can be rotated so as to impose a separating force on any analyte present on analyte receiving portion 101. In some embodiments, rotatable carrier 103 may be made of plastic or polymer and may be of similar manufacture to media/data discs (e.g., CDs, DVDs, Blu-ray discs, video game discs) used with conventional off-the-shelf media/data players and drives. In some embodiments, rotatable carrier 103 may be a media/data disc (e.g., CD, DVD, Blu-ray, video game disc, CD/DVD ROM disc) that analyte holding portion 101 may be attached to.

In some embodiments, rotatable carrier 103 may include a recess sized so as to receive analyte holding portion 101. For example, if analyte holding portion 101 has a size of 3 cm×2 cm, the dimensions of the recess of rotatable carrier 103 may be 3 cm×2 cm or slightly larger. In some embodiments, the friction between analyte receiving portion 101 and the recess of rotatable carrier 103 may be sufficient to removably secure analyte holding portion 101 when rotatable carrier 103 is rotated. In some embodiments, other mechanisms such as clips, protrusions in analyte holding portion 101 or rotatable carrier (with or without corresponding recesses in rotatable carrier 103 or analyte holding portion 101, respectively), tape, or other mechanisms may be used to removably secure analyte receiving portion 101 when rotatable carrier 103 is rotated.

In some embodiments, when inserted into a recess of rotatable carrier 103, analyte holding portion 101 may protrude above the plane of an upper surface of rotatable carrier 103. In some embodiments, when inserted into a recess of rotatable carrier 103, an upper surface of analyte receiving portion 101 may be flush or below the plane of the upper surface of rotatable carrier 103.

In some embodiments, analyte holding portion 101 need not be inserted into a recess of rotatable carrier 103, but simply may be removably secured to an upper surface of rotatable carrier 103 using, for example, adhesive tape. In some embodiments, analyte holding portion 101 may be an integral part of rotatable carrier and therefore not removable therefrom (e.g., analyte receiving portion 105, separation channel 107, analysis portion 111, and/or end portion 113 maybe integrated into a planar rotatable carrier 103).

In some embodiments, rotatable carrier 103 may include a transparent area that may be aligned with analysis portion 111 of analyte holding portion 101 (or other portion of analyte holding portion 101, e.g., along separation channel 107) that enables light (or other electromagnetic radiation) to be shone through rotatable carrier 103 and therefore through analysis portion 111 for the purpose of spectrographic or other analysis of the analyte (or a separated component thereof) in analyte holding portion 101. In some embodiments, the transparent area may be in a recess of rotatable carrier that receives and holds analyte holding portion 101 and therefore self-aligns with analysis portion 111 when analyte receiving portion 101 is placed within the recess. In some implementations, the recess may include an open bottom or other opening configured so as to enable light (or other electromagnetic radiation) to reach analysis portion 111 while still supporting and/or securing analysis holding portion 101 within rotatable carrier 103.

In some embodiments, rotatable carrier 103 may also include an engagement portion 115 that engages with a rotational actuator. In some embodiments, the rotational actuator may be part of a commercially available media/data disc player, such as, for example, a conventional compact disc (CD) player; a digital video disc (DVD) player; a blu-ray player; a CD and/or DVD ROM drive in a personal computer, laptop computer, or other computer; a disc drive of a video gaming system, or any other off-the-shelf/commercially available media or data player that is capable of rotating media or data discs (e.g., CDs, DVDs, blu-ray discs, CD ROM discs, DVD ROM discs, video game discs, etc.). Accordingly, rotatable carrier 103 may be or may be sized according to media/data discs usable with the media/data player that serves as or includes the rotational actuator. In some embodiments, rotatable carrier 103 may be sized differently from discs typically used with such a media/data player but may still be compatible with the media player. For example, business card-sized/shaped discs or discs of other configurations are usable with various CD/DVD ROM drives.

Figure 2:
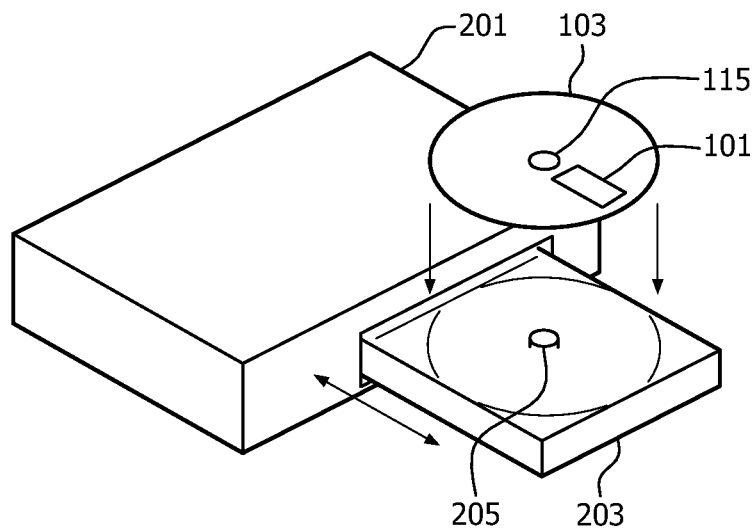
FIG. 2 is an example of a system for separation of a heterogeneous analyte, according to various embodiments of the invention.

Given that rotatable carrier 103 may be sized according to discs compatible with a media player used as or including a rotational actuator, in some embodiments, engagement portion 115 of rotatable carrier 103 may include an opening in rotatable carrier 103 that engages with a corresponding protrusion of the rotational actuator. FIG. 2 illustrates a rotational actuator 201 (e.g., a DVD player) that has a receiving tray 203 that may slide into and out of the body of rotational actuator 201. Receiving tray 203 may include an engagement portion/protrusion 205 that engages with corresponding engagement portion 115 of rotatable carrier 103. In some embodiments, the engagement portion of a rotational actuator may be completely internal to the rotational actuator. For example, some media players (i.e., rotational actuators) have a receiving tray without an engagement portion thereon, while some media players or disc drives may have an opening or slot into which discs may be inserted. In these instances, the engaging portion of the media player may be engaged to the rotatable carrier after a disc has been inserted fully into the player. In some implementations, the engagement portion of a rotational actuator may not be a protrusion that engages with engagement portion 115 of rotatable carrier 103, but may include another type of engagement portion such as, for example, those that use suction, friction, or other mechanism to rotate rotatable carrier 103.

In some embodiments, when engagement portion 115 of rotatable carrier 103 is engaged by a corresponding engagement portion/protrusion of the rotational actuator and analyte holding portion 101 is secured in rotatable carrier 103, rotational actuator (e.g., a CD player) may rotate its engagement portion/protrusion thereby causing rotatable carrier 103 to rotate (e.g., in the direction of arrow 117 of FIG. 1) and therefore applying a centrifugal force ($F_c = m\omega^2 r$) outward from the center of rotation (which, in FIGS. 1 and 2 would be the center of engaging portion 115). This centrifugal force acts to separate heterogeneous analytes in analyte holding portion 101 into at least two components. In instances wherein a sample of blood is used, separation of red and white blood cells (or "hematocrit") can be achieved in time scales ranging from seconds to a few minutes by the application of as small a force as 5 g. As commercially available off-the-shelf consumer electronic products (e.g., CD/DVD/blu ray players or drives) are capable of rotation speeds ranging from 500 rpm to 10,400 rpm (which translates to a maximum of about 1200 g) these products can be used as rotational actuators enabling the separation of whole blood into two or more components, namely, plasma and hematocrit (red and white blood cells). For example, the centrifugal force on a separation channel 1 cm away from the center of rotation that is rotated at 1200 rpm provides a separation force of about 15 g. This is beyond the 5 g minimum that enables separation of red and white blood cells from blood plasma.

One or more of the separated components may then be subject to analysis to determine one or more characteristics thereof. For example, in some embodiments, a rotational actuator may include one or more optical components that enable analysis of characteristics of an analyte within analyte holding portion 101. For example, the optics of conventional off-the-shelf media players or disc drives may be used to obtain absorbance characteristics of separated analyte components. The analog signal measured by the photodiode of a media player may be used to derive absorbance measurements for a separated component of an analyte. In a regular media player or disc drive operation, analog (raw) data is digitized and error correction codes are applied before the data is streamed out. For use in absorbance measurements with the systems, devices, and methods herein, the raw analog data from the disc drive may be used to derive the absorbance measurements of the analyte. For example, in some embodiments, the absorbance can be calculated by taking the ratio of the analog signal level received from analyte in analysis portion 111 into the analog signal level from a reference region on rotatable carrier 103. In some embodiments, one or more reference or look-up tables may be used to determine characteristics of analyte/sample components using this ratio. Accordingly, the media player/disc drive can be converted to an integrated bioanalytical device which can perform microfluidics and diagnostic functions simultaneously.

Figure 6:
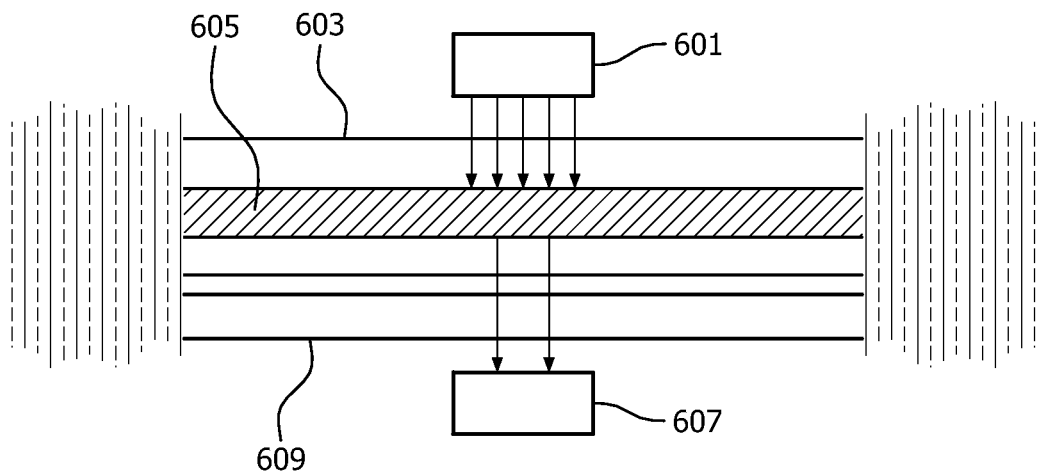
FIG. 6 is an example of at least a portion of a system for separation of a heterogeneous analyte, according to various embodiments of the invention.

FIG. 6 illustrates the use of optical components with an analyte holding portion and rotatable carrier. FIG. 6 illustrates an EM emitter 601, which emits light that travels perpendicularly through the planar surface of a portion of an analyte holding portion 603 that has an analysis portion 605 (which may be part of a separation channel of analyte holding portion 603) having an analyte or separate component thereof therein (e.g., blood plasma). Certain wavelengths of the emitted light may pass through the analyte or separated component thereof, and may be detected at a photodetector 607. The data regarding the detected light may be used to determine what wavelength of the emitted light was absorbed by the analyte or separated component thereof and therefore may be used to determine one or more characteristics of the analyte or separated component thereof. In some embodiments, wherein an analyte holding portion is carried in a rotatable carrier, the light may pass through a portion the rotatable carrier (labeled in FIG. 6 as item 609) prior to being detected by photodetector 607.

In some embodiments, optical analysis may be performed with optical components separate from a rotational actuator (e.g., a separate spectrograph). In some embodiments, a separated component may be subject to other analysis such as, for example, chromatographic or other analysis. In some embodiments, separated components of an analyte may be used for non-spectrographic testing (e.g., colormetric, fluorescence, etc.).

Figure 3:
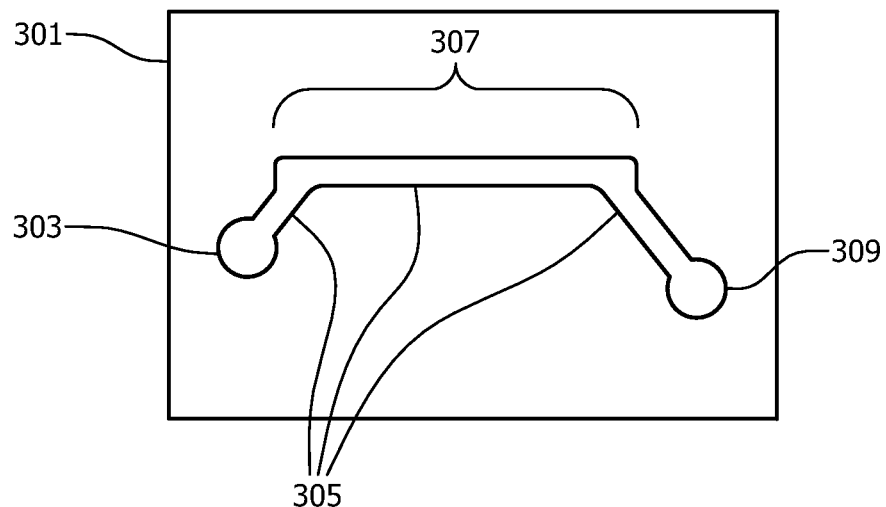
FIG. 3 is an example of an analyte holding portion, according to various embodiments of the invention.

In some embodiments, an analyte holding portion that may be used with the systems and methods described herein may have several configurations. Alteration of separation channel geometry or other characteristics may enable or enhance different characteristics or uses. For example, FIG. 3 illustrates an analyte holding portion 301 that enables optical probing in-plane with the plane of analyte holding portion 301 (as opposed to perpendicular with the plane of an analyte holding portion as illustrated in FIG. 6) with variable path length. Analyte holding portion 301 includes an analyte receiving portion 303, a separation channel 305 (including an analysis portion 307), and an end portion 309. The use of in-plane optical probing may require an EM emitter and photodetector arranged on opposite ends of analysis portion 307 so as to emit EM radiation through the separated analyte and detect absorbance. In some embodiments, the component elements of analyte holding portion 301 may be microfluidic in nature. For example, in some embodiments, separation channel may have cross sectional dimensions of 1 mm×1 mm and 10 mm in length. Other dimensions may be used.

Figure 4:
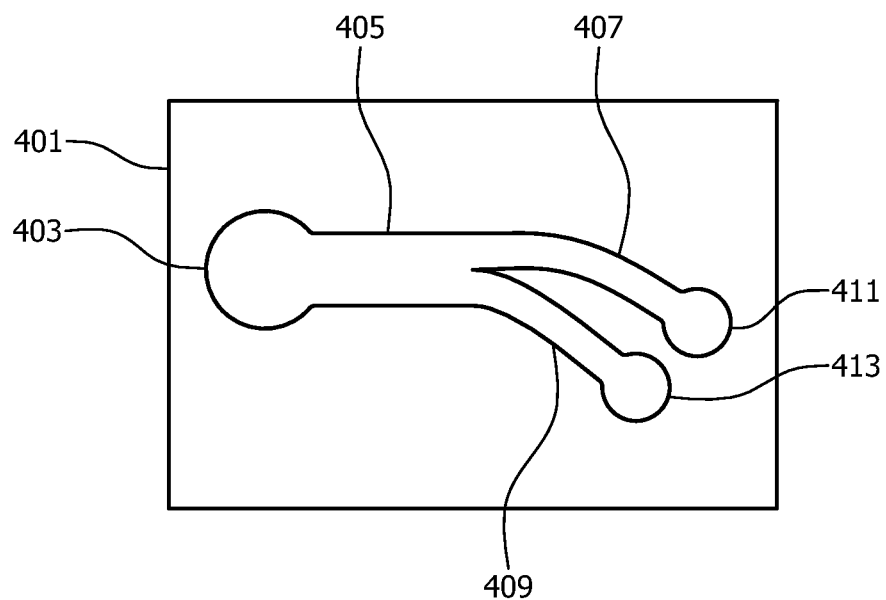
FIG. 4 is an example of an analyte holding portion, according to various embodiments of the invention.

FIG. 4 illustrates an analyte holding portion 401, which may enable separation as well as collection of a sample constituent for further use or analysis. Or example, if the sample analyte is blood, analyte holding portion 401 may enable not only separation of plasma from whole blood, but also may enable collection of plasma for use in a colormetric assay, separation of some specific plasma proteins, distribution for further testing, or for other purposes. Accordingly, analyte holding portion 401 may include an analyte receiving portion 403 that is larger than those illustrated in FIG. 1 or 3, so that more blood (or other fluid) may be loaded therein so that the fraction of collected plasma (or other fraction) is larger. For example, in some embodiments, analyte receiving portion may be sized to as to receive a volume of analyte (sample) that is 1-2 ml or larger. Analyte holding portion 401 may also include a separation channel 403 and branch channels 407 and 409 that lead to reservoir end portions 411 and 413 respectively. In some embodiments, analyte holding portion 401 may include constituent components that are microfluidic in size. For example, separation channel 403 and each of branch channels 407 and 409 may have cross-sectional dimensions of 1 mm×1 mm. Other dimensions may be used. Upon application of a separation force, red blood cells may be separated into branch channel 407 and therefore be collected in reservoir end portion 411, while plasma may be separated into branch channel 409 and therefore be collected in reservoir end portion 413. Due to centrifugal force, the hematocrit, being heavier, will be forced into the upper wall of separation channel 403 (i.e., towards branch channel 407). Accordingly, upper branch channel 407 will include the heavier red and white blood cells, while lower branch channel 409 will include only the plasma. In some embodiments, the length of separation channel 403 can determine the efficiency of plasma separation. For example, in some embodiments, separation channel 403 may have a length of greater than 10 mm. In some embodiments, reservoir end portion 413 may include an opening so that plasma may be removed for further use.

Figure 5:
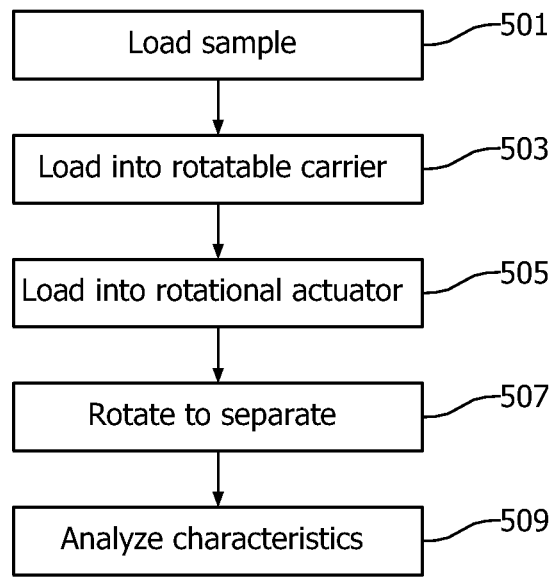
FIG. 5 is an example of a method for separation of a heterogeneous analyte, according to various embodiments of the invention.

In some embodiments, methods for separation of a heterogeneous analyte may be provided. FIG. 5 illustrates a process 500, which is an example of a process for separation of a heterogeneous analyte. Process 500 may include an operation 501, wherein a sample of heterogeneous analyte may be loaded into the analyte receiving portion of an analyte holding portion (e.g., analyte receiving portions 105, 303, or 403 of analyte holding portions 101, 301, or 401, respectively). In some embodiments, the heterogeneous analyte may be or include blood. In some embodiments, the blood sample may be obtained from a patient using a needle, cannula, or other implement, to extract the blood from a tissue of a patient. In some embodiments, the blood may have been previously obtained from the patient and transferred to a container wherefrom the blood may be obtained for deposition into the analyte receiving portion. Heterogeneous fluids other than blood may be used with the systems and methods of the invention.

In an operation 503, the analyte holding portion may be loaded into or onto a rotatable carrier (e.g., rotatable carrier 103). In some embodiments, the rotatable carrier may be or may be sized similar to a media/data disc for use in a media/data disc player. In some embodiments, the rotatable carrier may have a recess or other area specifically sized and shaped so as to receive the analyte holding portion. Accordingly, in these instances, loading the analyte holding portion into the rotatable carrier may include placing and/or securing the analyte holding portion into the recess or other area on the rotatable carrier. In some embodiments, loading the analyte holding portion onto the rotatable carrier may include securing the analyte holding portion to the rotatable carrier with, clips, tape, adhesive, or other securing elements.

In an operation 505, the rotatable carrier may be loaded onto a rotational actuator (e.g., rotational actuator 201). In some embodiments, the rotational actuator may be a commercial off-the-shelf media/data player that receives and rotates media/data discs such as, for example, a CD player, a DVD player, a Blu-ray player, a CD ROM drive, a DVD ROM drive, a video gaming system that utilizes game discs, or other such media/data player. Accordingly, the rotatable carrier used may be or may be sized and otherwise configured the same as or similar to the media/data discs used with such media/data player (e.g., a CD, DVD, Blu-ray disc, CD ROM disc, DVD ROM disc, video game disc, etc.). In some embodiments, loading the rotatable carrier onto the rotational actuator includes engaging a protrusion or other engaging portion with a correspondingly shaped engaging portion of rotatable carrier.

In an operation 507, the rotational actuator may cause the rotatable carrier to rotate, thereby applying a separating centrifugal force onto the analyte in the analyte holding portion and causing the analyte to separate into two or more components along a separation channel (e.g., separation channel 107, 305, or 405) of the analyte holding portion. Accordingly, more massive portions of the heterogeneous analyte will move farther down the separation channel and less massive portions will move less far down the separation channel, thereby at least partially separating the heterogeneous analyte into at least two components. In some embodiments, wherein the heterogeneous analyte is blood, the centrifugal separation force will separate the blood into heavier (more massive) red and white blood cells or hematocrit, and blood plasma.

In an operation 509, one or more characteristics of one or more of the separated components may be analyzed. In some embodiments, analyzing a characteristic of one or more of the separated components may include utilizing an optical portion of a media/data player used as the rotational actuator to expose one of the separated components in the analyte holding portion to light (or other electromagnetic radiation) and measuring the absorption spectrum of light passing through the separated component. In some embodiments, the separated component may be exposed to light during rotation of the rotating component by the rotational actuator. In some embodiments, analyzing a characteristic of one or more of the separated components may include removing the rotatable carrier (or analyte holding portion) from the rotational actuator and placing the analyte holding portion (or a separated component therefrom) into a separate analysis apparatus (e.g., a separate spectrograph), a chromatograph, colorimetric strip, or other analysis apparatus.

The systems described herein are exemplary system configurations. Other configurations may exist. Those having skill in the art will appreciate that the invention described herein may work with various configurations. Accordingly, more or less of the aforementioned system components may be used and/or combined in various embodiments. Furthermore, various operations of the methods described herein, while described in a particular order, may be performed in different orders as would be appreciated by those having skill in the art. In some embodiments, more of less of the described operations may be used.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system for separation of a heterogeneous analyte, comprising:
    an analyte holding portion including:
        a microfluidic separation channel; and
        an analyte receiving portion coupled to the microfluidic separation channel, the analyte receiving portion being configured to receive a volume of analyte;
    a rotatable carrier configured to removably engage and hold the analyte holding portion; and
    a media or data disc player or a media or data disc drive comprising:
        a rotational actuator configured to removably engage the rotatable carrier and to rotate the rotatable carrier so as to apply a centrifugal force to the volume of analyte such that the analyte is separated into at least two components within the microfluidic separation channel; and
        optics for spectrographic analysis of at least one of the separated analyte components while the rotatable carrier is rotating relative to the optics.

2. The system of claim 1, wherein the rotatable carrier is sized as digital media or data disc.

3. The system of claim 1, wherein the analyte holding portion comprises a planar chip that is removably securable into a correspondingly sized recess of the rotatable carrier.

4. The system of claim 1, wherein the analyte includes blood, and wherein separation of the analyte includes separating red and white blood cells from blood plasma in the blood.

5. The system of claim 4, wherein the analyte holding portion further includes an analysis portion, wherein at least a portion of the blood plasma is located in the analysis portion after separation, and wherein the plasma in the analysis portion is subjected to the spectrographic analysis to determine at least one characteristic of the plasma.

6. The system of claim 1, wherein the optics for spectrographic analysis of the at least one separated analyte component are configured to obtain absorbance characteristics of the at least one separated analyte component, the absorbance characteristics being calculated based on a ratio of (1) an analog signal level received from the at least one separated analyte component in an analysis portion of the analyte holding portion to (2) an analog signal level received from a reference region on the rotatable carrier.

7. The system of claim 1, wherein light emitted from the optics passes through the at least one separated analyte component and is detected at a photodetector of the system.

8. The system of claim 1, wherein the analyte holding portion further includes an analysis portion, the analysis portion comprising an enlarged area of the microfluidic separation channel, wherein the enlarged area has dimensions that are larger than dimensions of the microfluidic separation channel.

9. The system of claim 1, wherein the volume of the analyte is in a range between 50 and 100 μL.

10. The system of claim 1, wherein the analyte holding portion is removably engaged via clips, tape, or adhesive.

11. The system of claim 1, wherein the microfluidic separation channel has cross-sectional dimensions of about 1 mm×1 mm or a cross-sectional diameter of about 1 mm.

12. The system of claim 1, wherein a length of the microfluidic separation channel is 5 cm or less.

13. The system of claim 1, wherein the analyte holding portion includes a reservoir coupled to the microfluidic separation channel at an opposite end of the microfluidic separation channel with respect to the analyte receiving portion.

* * * * *